United States Patent
Baumann et al.

(10) Patent No.: US 7,838,306 B2
(45) Date of Patent: Nov. 23, 2010

(54) ADSORBENT HAVING DIFFERENTLY MODIFIED SURFACE AREAS, METHOD FOR THE PRODUCTION THEREOF AND USE OF THE SAME

(75) Inventors: Hanno Baumann, Aachen (DE); Franz-Josef Gerner, St. Wendel (DE); Michael Hoffmann, Eschweiler (DE); Roland Horres, Stolberg (DE); Andreas Kokott, Bad Steben (DE); Hans-Peter Leinenbach, Tholey (DE); Gunter Mathar, Stolberg (DE); Wolfgang Metzger, Saarbrucken (DE); Veit Otto, St. Wendel (DE); Walter Ruger, Schenklengsfeld (DE); Martin Schimmel, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 859 days.

(21) Appl. No.: 10/380,193

(22) PCT Filed: Sep. 14, 2001

(86) PCT No.: PCT/EP01/10678
§ 371 (c)(1),
(2), (4) Date: Sep. 12, 2003

(87) PCT Pub. No.: WO02/22253
PCT Pub. Date: Mar. 21, 2002

(65) Prior Publication Data
US 2004/0202783 A1 Oct. 14, 2004

(30) Foreign Application Priority Data
Sep. 14, 2000 (DE) .................. 100 45 434

(51) Int. Cl.
*G01N 33/543* (2006.01)
*G01N 33/544* (2006.01)

(52) U.S. Cl. .............. 436/523; 436/528; 436/535; 436/541

(58) Field of Classification Search ........... 530/412, 530/413, 415, 381, 402, 403, 812; 436/531, 436/528, 85, 539, 823, 824, 523, 7.1
See application file for complete search history.

(56) References Cited

U.S. PATENT DOCUMENTS

| | | | | |
|---|---|---|---|---|
| 3,770,631 A * | 11/1973 | Fekete et al. | ............... | 530/380 |
| 4,544,485 A | 10/1985 | Pinkerton | | |
| 4,694,044 A * | 9/1987 | Kiniwa | ............... | 525/178 |
| 5,061,789 A * | 10/1991 | Moller et al. | ............... | 530/381 |
| 5,773,384 A | 6/1998 | Davankov | | |
| 6,325,939 B2 * | 12/2001 | Strom et al. | ............... | 210/645 |

FOREIGN PATENT DOCUMENTS
DE 198 56 387 6/2000

(Continued)

OTHER PUBLICATIONS

Sarobe et al. Nephelometric assay of immunoglobulin G chemically bound to chloromethyl styrene beads. Polymers for Advanced Technologies 1996, vol. 7, pp. 749-753.*

(Continued)

*Primary Examiner*—Shafiqul Haq
(74) *Attorney, Agent, or Firm*—Kenyon & Kenyon LLP

(57) ABSTRACT

An adsorbent for whole blood in the form of essentially spherical non-aggregated particles. The adsorbent comprises a porous carrier material having an average pore size of $\leq 1.5$ µm, whereby a maximum of 50% of the pore volume may be in pores having a pore size of >1.5 µm, whereby the outer surfaces of the porous carrier material have at least one surface modification $M_1$ so that the outer surface essentially does not interact with blood cells, and the inner surfaces of the porous carrier material, e.g., the surfaces of the pores of the porous carrier material, have at least one surface modification $M_2$ which interacts with substances present in blood.

17 Claims, 2 Drawing Sheets

FOREIGN PATENT DOCUMENTS

| | | |
|---|---|---|
| EP | 0 106 769 | 4/1984 |
| EP | 0 295 809 | 12/1988 |
| FR | 2 653 034 | 4/1991 |
| GB | 2 113 226 | 8/1983 |
| JP | 63 017906 | 1/1988 |
| JP | 1123145 | 5/1989 |
| JP | 3107759 | 5/1991 |
| JP | 05 302917 | 11/1993 |
| JP | 200008847 A * | 3/2000 |
| WO | WO 88/01514 * | 3/1988 |

OTHER PUBLICATIONS

Hauser et al. Nucleotide sequence of the streptococcal pyrogenic exotoxin type B gene and relationship between the toxin and the streptococcal proteinase precursor. J. Bacteriol. 1990, vol. 171, No. 8, pp. 4536-4542.*

Peterson et al. Physical properties of short- and long-O-antigen-containing fractions of lipopolysaccharide from *Escherichia coli* 0111:B4, J. Bacteriol 1996, vol. 165, No. 1, pp. 116-122.*

Davankov et al, "Structure and Properties of Hypercrosslinked Polystyrene—The First Representative of a New Class of Polymer Networks," Reactive Polymer, 13 (1990) 27-42.

Aiken, "Evaluation of Ultrafiltration for Determining Molecular Weight of Fluvic Acid," Environ. Sci. Technol., 1984, 18 (12) 978-981.

Gejyo et al., "β2-microglobulin: A new form of amyloid protein associated with chronic hemodialysis," Kidney International, vol. 30 (1986), pp. 385-390.

CRC Handbook of Chemistry and Physics, p. 3-520 (Lide ed.,CRC Press, 89th ed., 2008-2009).

Fantl et al., "Molecular weight of human fibrinogen derived from phosphorous determinations," Biochem J., Sep. 1965; 96(3): 886-889.

McGraw-Hill Concise Encyclopedia of Science and Technology, p. 898 (Parker ed., 4th ed.), 1998.

Fisher et al. "A Genetic Determinant of the Phenotypic Variance of the Molecular Weight of Low Density Lipoprotein," Proc. Nat. Acad. Sci. USA, vol. 72, No. 6, pp. 2347-2351, Jun. 1975.

* cited by examiner

ADSORBENT HAVING DIFFERENTLY MODIFIED SURFACE AREAS, METHOD FOR THE PRODUCTION THEREOF AND USE OF THE SAME

This application is a National Stage application of PCT International Application No. PCT/EP01/10678, filed on Sep. 14, 2001 and claims foreign priority benefits to German Patent Application No. 100 45 434.8-43, filed on Sep. 14, 2000.

FIELD OF THE INVENTION

The present invention relates to an adsorbent for whole blood, and in particular to an adsorbent in the form of essentially spherical non-aggregated particles. Furthermore, the present invention relates to a method of producing such an adsorbent and the use of this adsorbent.

BACKGROUND

Adsorbents are widely used in medical technology. Adsorbers with adsorbents which remove low-density lipoproteins (LDL) from blood or blood constituents or reduce the concentrate thereof, such as those known from German Patent No. 39 32 971 ('DE '971') are known. DE '971 describes an adsorbent material as an organic carrier with a fixed particle size and an exclusion limit, carrying a functionality at its surface to which the LDL molecule binds.

There are LDL adsorbers made of porous polymethacrylate particles coated with polyacrylic acid (PAA), where PAA is present in bound form on the outer surface bordering the particles as well as on the inner surface enclosing the pores. Since blood cells have only minor interactions with PAA, such an adsorbent is suitable for whole blood, e.g., the adsorbent particles allow blood cells to pass through without interacting with them, e.g., without activating, binding or damaging them. Thus, according to this method all the blood may be passed through the adsorber without prior separation of the blood cells. The LDL is separated out here through a size exclusion mechanism and not by way of a specific binding of LDL to a functional group adhering to the carrier.

It is not typical for an adsorbent to be compatible with whole blood, because the carrier material normally leads to complement activation and/or triggers platelet aggregation and adhesion.

Whole blood compatibility depends in particular on the coating used with functional groups. When using certain functional groups known in the related art, it is impossible to produce adsorbers that are compatible with whole blood because they interact with the blood cells. One example of this is an adsorber for binding immune complexes, where the adsorber carries the protein C1q as a functional group on its surface. The protein enters into an interaction with immunoglobulins and may remove them from their solutions. However, blood cells, in particular platelets, also have a binding site with the protein C1q, and they are also bound to such adsorbents. Thus, whole blood cannot pass through these adsorbents unimpaired. The same problems also occur with so-called fibrinogen absorbers.

In such cases, the blood cells are first separated from the blood plasma, whereupon only the plasma is passed through the adsorber. After separation of the immune complexes by binding to the C1q protein, the blood cells are combined again with the purified blood plasma. This procedure is complicated and is a burden for the patient as well as being a high-risk procedure.

The whole blood adsorbents described in the literature (e.g., Dräger et al., *Eur. J. Clin. Invest.* 1998, 28 (12); U.S. Pat. No. 5,476,715 A) consist of particles so large that they form interspaces in which the blood cells can move. Furthermore, the particles have pores leading to an internal surface. These pores are large enough that even macromolecules can penetrate into them. However, these pores are so small that blood cells are prevented from penetrating into them. Thus, blood cells come in contact only with the outer surface of the particles. Furthermore, according to European Patent No. 0 424 698, these particles must be as spherical and unaggregated as possible to have a "smooth" and inert outside, so that the platelets will slide past them.

German Patent Application 198 42 785 A1 describes porous materials whose surfaces are chemically functionalized so that the outer surface of the porous materials is electroneutral and hydrophilic, while the inner surface may even be provided with so-called functional ligands. Materials compatible with whole blood are not described there, however. These porous materials are produced by first introducing epoxy groups into a porous base carrier, whereby both the pore surfaces and the outer surface of the base carrier are functionalized with epoxy groups, and then the epoxy groups are catalytically opened by reaction with a nucleophile. In this process, a particulate catalyst having a particle size larger than the average pore diameter of the porous base carrier is used, so that no reaction can take place in the pores. Then the remaining epoxy groups at the pore surfaces are converted by introducing functional ligands. However, using a particulate catalyst entails some considerable disadvantages, because it is difficult to separate the particulate catalyst from the coated carrier material. Furthermore, a reaction may and can take place only at the points of contact between the catalyst particles and the carrier material particles, so that very long reaction times and extensive stirring are necessary to achieve an approximately complete reaction at the surface. Furthermore, prolonged stirring can result in abrasion of the catalyst particles, so the adsorber may become contaminated with catalyst residues. Furthermore, when magnetic catalyst particles are used, the possibility of catalyst particles remaining in the adsorbent cannot be ruled out. However, these catalyst particles may lead to problems, especially in purifying whole blood, due to interactions with the constituents of blood, so that such a catalyst is not compatible with whole blood.

Thus, one object of the present invention is to provide an adsorbent which is compatible with whole blood and carries groups in locations that are not accessible to blood cells, these groups being capable of interacting with substances to be separated from the blood. Furthermore, another object of the present invention is to provide a method with which such an adsorbent can be produced easily and economically.

SUMMARY OF THE INVENTION

The present invention, in accordance with one embodiment thereof, is directed to an adsorbent for whole blood which is provided in the form of essentially spherical non-aggregated particles. The adsorbent comprises a porous carrier material having an average pore size of $\geq 1.5$ μm, whereby a maximum of 50% of the pore volume may be in pores having a pore size of $>1.5$ μm, whereby the outer surfaces of the porous carrier material have at least one surface modification $M_1$ so that the outer surface essentially does not interact with blood cells, and the inner surfaces of the porous carrier material, e.g., the surfaces of the pores of the porous carrier material, have at least one surface modification $M_2$ which interacts with substances present in blood.

DETAILED DESCRIPTION

Figure 1:
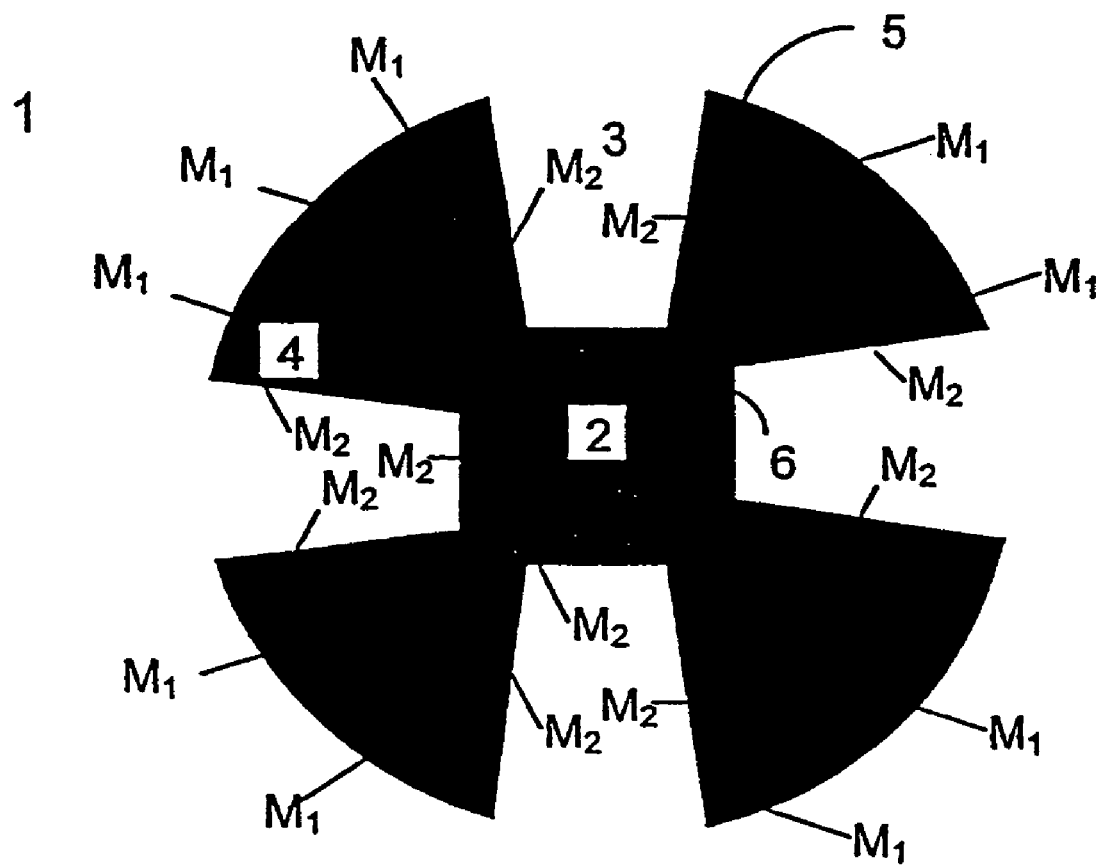
FIG. 1 illustrates a schematic cross-section of an adsorbent particle, according to one ebodiment of the present invention.

FIG. 1 illustrates schematically a cross section through an embodiment of an adsorbent particle 1 according to one embodiment of the present invention, having a carrier material 2 with pores 3 and modifiable binding sites 4 as well as surface modifications $M_1$ and $M_2$ bound thereto. The pores 3 of carrier material 2 are surrounded by "inner" surfaces 6 which have surface modifications $M_2$ bound to them. The binding sites on the "outer" surface 5, e.g., the surface surrounding adsorber particles 1, are occupied by surface modifications $M_1$ which are different from the surface modifications $M_2$ on the inner surfaces 6.

Figure 2:
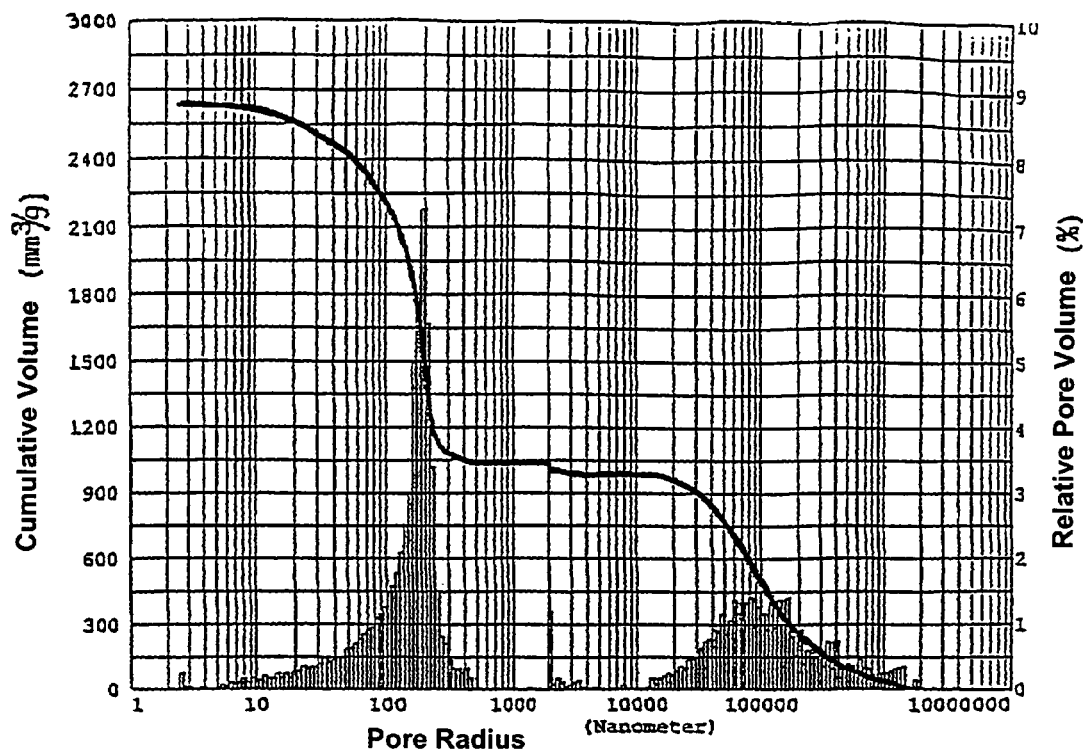
FIGS. 2 and 3 illustrate pore size distributions measured on an adsorbent, according to various embodiments of the present invention.
Figure 3:
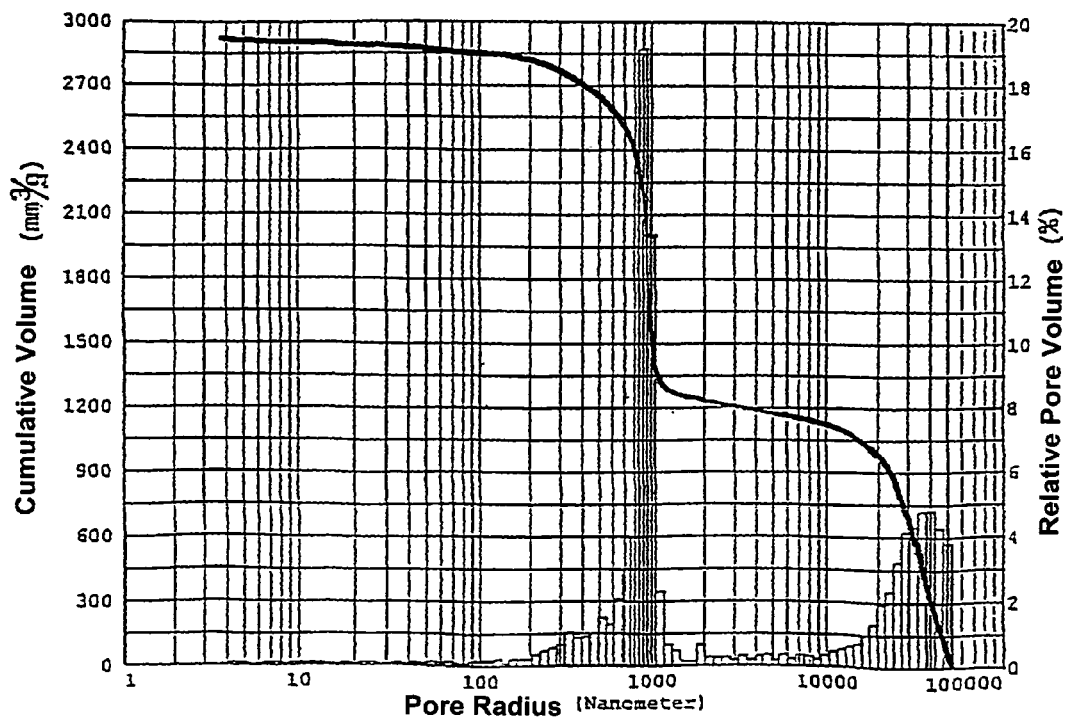

FIGS. 2 and 3 show, for example, two pore size distributions which were measured on an adsorbent according to one embodiment of the present invention by the method analogous to DIN 66,133 as described below.

Herein, the term "outer surfaces" of a particle is understood to refer to the surface enclosing the particle, and the term "inner surfaces" of a particle is understood to refer to the surfaces which enclose the pores of the particle, e.g., the surfaces of the pores of the particle.

The term "interaction" according to this invention includes activation, binding, reaction and/or damage of substances and/or cells contained in whole blood. According to one embodiment of the present invention, a selective interaction is preferred. According to another embodiment, the interaction may also be specific.

The adsorbent according to one embodiment of the present invention is particulate. The particles of the adsorbent according to this invention are essentially spherical and are not aggregated. Spherical particles in contrast with irregularly shaped particles or irregularly shaped aggregates of particles have the advantage that they do not retain blood particles such as platelets in an undesirable manner.

The porous carrier material of the adsorbent according to one embodiment of the present invention has an average pore size and/or an average pore diameter with a value of $\leq 1.5\,\mu m$, preferably $\leq 1.0\,\mu m$, with a maximum of 50% of the pore volume being in the form of pores having a pore size of $>1.5\,\mu m$. The maximum average pore size of $1.5\,\mu m$ is determined by the size of the smallest blood cells, which have a diameter of approximately $2\,\mu m$. A maximum average pore size such as that defined according to the present invention ensures that essentially no blood cells can penetrate into the pores. If only very small particles or dissolved particles are to be separated from blood, it is preferable to select a porous carrier material having a lower average pore size, e.g., $1\,\mu m$, $0.5\,\mu m$ or $0.3\,\mu m$.

According to this invention, the average pore size can be determined by mercury intrusion (mercury porosimetry) analogous to DIN 66,133. This method is based on measurement of the mercury volume injected into a porous solid as a function of the selected pressure. A non-wetting fluid such as mercury will penetrate into a porous system only under pressure. The pressure to be applied is inversely proportional to the inside diameter of the pore openings. This detects pores into which mercury can penetrate at the applied pressure. For cylindrical pores, the relationship between the pore radius $r_p$ and the pressure p is given by the Washburn equation:

$$r_p = -\frac{2 \cdot \sigma}{p} \cos\theta$$

where $\sigma$ is the surface tension of mercury [N/m] and $\theta$ is the wetting angle of mercury on the specimen, measured through the liquid phase. In deviation from DIN 66,133, a fixed value of 141.3° is used for the wetting angle, and interparticulate volumes are not taken into account in determination of the average pore size. FIGS. 2 and 3 show as examples the determination of the average pore volume of two porous carrier materials, which can be used according to the present invention. The interparticulate volumes are represented by the right peak, which begins at values above approximately $10\,\mu m$. The left peak shows the distribution of open pores. FIG. 2 shows a carrier material having a relatively small average pore size of approximately 200 nm. FIG. 3 shows a carrier material having a larger average pore size of approximately $1\,\mu m$.

Furthermore, the adsorbent particles preferably have a particle size of $50\,\mu m$ to $500\,\mu m$, more preferably from $100\,\mu m$ to $300\,\mu m$. When used in an extracorporeal circulation with whole blood, the particles of the adsorbent should have a particle size of at least $50\,\mu m$, because the largest blood corpuscles, e.g., blood cells present in whole blood, have a diameter of $20\,\mu m$. Thus, the screen which retains the adsorbent may have a mesh of at least $25\,\mu m$, preferably at least $40\,\mu m$, to allow all the blood cells to pass through. Furthermore, the interspace between the particles in the columns packed with adsorbent particles $50\,\mu m$ or more in size is sufficient to allow the blood cells to pass through. Furthermore, in selecting the screen material, it is important for the mesh width to be smaller than the diameter of the smallest adsorber particles.

The adsorbent according to one embodiment of the present invention includes a porous carrier material. It is possible here to start with a prepared porous particulate carrier material whose outer and inner surfaces have been modified according to the present invention. Suitable materials according to this embodiment include, for example, carrier materials such as glasses, carbohydrates, Sepharose, silica or organic carrier materials such as copolymers of acrylates or methacrylates and polyamides. The carrier material in this embodiment is preferably made of an organic material, especially preferably copolymers derived from (meth)acrylate esters and/or (meth) acrylamides. They preferably have epoxy groups. The term "(meth)acryl" is understood to refer to both the corresponding acrylic compounds as well as the corresponding methacrylic compounds.

However, instead of starting with already prepared particles as the carrier material, it is also possible to produce porous particles based on a polymer starting from the corresponding monomers and to modify the inner and outer surfaces of the porous polymer particles obtained in this way.

The porous carrier material to be used according to one embodiment of the present invention has modifiable binding sites on its outer and inner surfaces, which can be used for surface modifications $M_1$ and/or $M_2$. An especially preferable binding site is a strained heterocyclic system as a functional group capable of binding additional functional groups to a carrier material while undergoing ring opening, in particular nucleophilic ring opening, through direct covalent binding, and thus the material has such functional groups as the surface modification $M_1$ and/or $M_2$. The carrier material especially preferably contains oxirane groups, e.g., epoxy groups as binding sites for such functional groups.

A crosslinked random copolymer obtained by polymerization of ethylene glycol di(meth)acrylate and glycidyl (meth) acrylate and/or allylglycidyl ether is preferred as the carrier material.

In the embodiment of the present invention, whereby a porous particulate carrier material such as glasses, carbohydrates, Sepharose, silica or organic carrier materials is provided in a first step, a preferred crosslinked random copolymer is produced by polymerization of the following monomer units:

(A) (meth)acrylamide in an amount of 10 to 30 percent by weight, (B) N,N'-methylene-bis(meth)acrylamide in an amount of 30 to 80 percent by weight, and (C) allylglycidyl ether and/or glycidyl (meth)acrylate in an amount of 10 to 20 percent by weight, each based on the total weight of the monomer units.

The network structure is preferably produced by suspension polymerization. Such a copolymer is commonly available under the brand name Eupergit C250L and Eupergit FE 162 from Röhm GmbH.

According to one embodiment of this invention, the term "surface modification" is understood to refer to a preferably organic terminal group, substance, compound and/or precursor compound suitable for binding to binding sites of a carrier material and which, when bound to a carrier material, has the ability to enter into a preferably selective interaction with certain substances or group of substances contained in a solution.

The outer surface of the particles of the carrier material has a surface modification $M_1$ which has essentially no interaction with blood cells, e.g., the outer surface of the particles is "smooth," e.g., inert with respect to blood cells.

Such surface modifications $M_1$ that are smooth with respect to blood cells are known in the literature. Surface modification $M_1$ according to the present invention is preferably the reaction product of the reaction of the binding sites on the surfaces with at least one poly(carboxylic acid), albumin, heparin, heparan sulfate, polyethylene oxide and block copolymers of PE and polypropylene oxide (PPO) and/or a polymyxin. Polyacrylic acid and heparin are especially preferred examples. The term poly(meth)acrylic acid and corresponding terms such as those used below denote compounds which can be derived from acrylic acid or methacrylic acid or a mixture thereof. Poly(meth)acrylic acids (PAA) are understood to be polymers of the formula $-(CH_2-C(H)(COOH))_n-$ and/or $-(CH_2-C(CH_3)(COOH))_n-$ obtained by radical polymerization of acrylic acid and/or (methyl)acrylic acid. However, poly(meth)acrylic acids are also accessible by hydrolysis of polymeric (meth)acrylic acid derivatives, such as esters, amides, nitriles. An especially suitable poly(meth)acrylic acid according to the present invention has a weight-average molecule weight of $10^2$ g/mol to $10^7$ g/mol, for example. Polymyxins are peptide antibiotics which are effective only against gram-negative bacteria. Polymyxin B refers to cyclopeptides having L-2,4-diaminobutyric acid groups and a D-amino acid.

According to one embodiment, surface modification $M_1$ may interact with substances other than blood cells. This is possible as long as surface modification $M_1$ no longer has any interactions with blood cells, but instead it only interacts selectively with other substances present in blood. According to this embodiment, the surface modification $M_1$ may thus be a functional surface modification.

Surface modification $M_2$ interacts with substances present in blood, so that only those substances which are small enough to penetrate into the pores, depending on the selected pore size, can come in contact with surface modification $M_2$. Thus, surface modification $M_2$ is a so-called functional surface modification, where functional surface modifications are understood to refer to, for example, separation effectors or even catalysts or enzymes. Separation effectors produce selective interactions, which may be used for chromatographic separations or other distribution methods such as liquid-liquid distribution.

Since the blood cells cannot penetrate into the pores and thus cannot come in direct contact with surface modifications $M_2$, it is thus possible to provide the inner surface of the adsorbent particles with a surface modification $M_2$ which is incompatible with blood cells.

The at least one surface modification $M_2$ preferably comprises at least one immunoadsorber present on the inner surface. The term "immunoadsorber" is understood according to the present invention to refer to a compound capable of binding, preferably specifically, to certain substances or substance groups by means of an immune reaction. Especially preferred immunoadsorber are those selected from the group comprising complement factor C1q, functional groups containing amines, peptides, antibodies such as monoclonal or polyclonal anti-fibrinogen antibodies or anti-fibrin antibodies and antigens such as synthetic AB blood group antigens as well as DNA and RNA or their mirror molecules.

When surface modification $M_1$ and/or $M_2$ involves functional groups, they may be bound covalently to the carrier material over a spacer. A "spacer" is understood to refer to organic bridge elements having various chemical structures and lengths with the help of which organic functional groups may be bound at the surface of a carrier material. Preferably, however, such functional groups as surface modifications $M_1$ and/or $M_2$ are bound directly to a surface of the carrier material without a spacer. Directly binding a functional group to the carrier material may eliminate one reaction step.

Thus, with a suitable surface modification $M_2$ on the inner surface of the adsorbent material, it is possible to separate substances present in whole blood if they have approximately the same diameter or preferably a smaller diameter than the selected average pore size of the porous carrier material. The average pore size is preferably selected for effective separation, so the pores are much larger than the particles to be separated.

The possibility of sterilizability, e.g., by gamma radiation, plasma treatment or ethylene oxide treatment (in particular, heat sterilizability at 121° C., for example) is important for use of such an adsorbent, because the blood may be returned to the patient after being treated, and it should not cause any sepsis or inflammation. Heat sterilizability at 121° C. and 1 bar pressure is preferred, if necessary in combination with a stabilizing pretreatment.

With the adsorbent according to the present invention, it is possible to separate substances present in blood from whole blood, even if surface modification $M_2$, which is required for the separation, would have a harmful interaction with blood cells, because the blood cells cannot penetrate into the pores of the adsorbent on the inside walls of which surface modification $M_2$ is located exclusively. This eliminates extracorporeal steps, such as the separation of blood cells, treatment of isolated plasma and combining the blood constituents, thereby increasing the biocompatibility of this method and further greatly reducing the risk of complement activation.

Eliminating extracorporeal steps shortens the treatment time and simplifies the method, thereby increasing the safety and well-being of the patient.

The present invention also relates to a method of producing an adsorbent, which includes the steps:

providing a porous particulate carrier material which has modifiable binding sites on the inner and outer surfaces, filling the pores of the carrier material with at least one medium which is liquid under the conditions of filling and is essentially not miscible (under the modification conditions) with a solution with which binding sites on the surfaces of the carrier material can be modified essentially completely, modifying the binding sites on the outer surfaces of the carrier material essentially completely to form at least one surface modification $M_1$, and optionally removing the medium from the pores, the medium being essentially not miscible (under the modification conditions) with a solution with which binding sites on the surfaces of the carrier material can be modified essentially completely.

Preferably after the step of essentially complete modification of the binding sites on the outer surfaces of the carrier material to form at least one surface modification $M_1$ or the step of removing the medium from the pores, where this medium is essentially not miscible (under the modification conditions) with a solution with which the binding sites on the surfaces of the carrier material can be modified essentially completely, the binding sites on the inner surfaces of the carrier material are modified to yield at least one surface modification $M_2$ with a reaction solution which is not capable of modifying the surface modifications $M_1$.

According to the step described above for filling the pores of the carrier material of one embodiment of the method according to the present invention, first the pores of the carrier material are filled with a medium that is liquid under the conditions of filling. This medium is essentially not miscible (under the modification conditions) with a solution capable of essentially complete modification of binding sites on the surfaces of the carrier material to form at least one surface modification $M_1$.

The phrase "a medium liquid under the conditions of filling" includes, according to the present invention, media that can be poured or otherwise introduced into the pores of a carrier material and can be removed from these pores again essentially completely, and which is essentially not miscible (under the modification conditions) with a solution capable of essentially complete modification of binding sites on the surfaces of the carrier material to form at least one surface modification $M_1$. Such media may consist of a single medium, mixtures of at least two media and/or solutions.

As a rule, the medium will be one that is liquid at room temperature. According to a special embodiment, however, the medium may also be gaseous at room temperature. Then the pores are filled, for example, at a reduced temperature and/or an elevated pressure, and the binding sites on the outer surfaces are modified under these conditions. This embodiment has the advantage that a medium which is gaseous at room temperature can be removed from the pores again especially easily. According to another embodiment, the medium may be solid at room temperature. Then the pores of the carrier material may be filled while heating, for example. This embodiment has the advantage that the pores are filled with the medium essentially permanently, e.g., for longer reactions.

In practice, this filling of the pores may be performed with a medium by, in the simplest case, immersing the particles of the porous carrier material in a medium that is liquid at room temperature and swelling them with this medium, so that air is displaced out of the pores of the carrier material essentially completely. Furthermore, the particles may also be placed in an airtight container, whereupon air is removed from the container and thus also from the pores of the porous carrier material by applying a vacuum, and then the medium is added to the particles in the evacuated container under conditions under which this medium is liquid.

After swelling of the particles, the excess liquid medium may be suctioned briefly with a suction filter, for example, to remove it from the carrier material particles without removing the medium present in the pores. Then the reaction solution for modifying the binding sites on the surfaces of the carrier material to yield a surface modification $M_1$ is added to the particles.

According to the present invention, the medium for filling the pores is essentially not miscible with this reaction solution (under the modification conditions). Thus, preferably a hydrophobic medium is used as the pore-filling and/or pore-forming medium during a modification $M_1$ of the outer surfaces and/or when using an aqueous reaction solution. Especially preferred media for use as the hydrophobic medium include those from the group consisting of linear or branched, cyclic or acyclic $C_1$- to $C_{20}$-alkanes such as pentane, hexane, heptane, octane, nonane, decane, cyclohexane and linear or branched, cyclic or acyclic $C_5$- to $C_{20}$-alkanols such as hexanol, octanol, decanol, undecanol and dodecanol, linear and branched, cyclic or acyclic $C_2$- to $C_{30}$-carboxylate esters and aromatic $C_6$- to $C_{20}$-hydrocarbons as well as mixtures thereof.

After filling the pores with a medium that is essentially not miscible (under the modification conditions) with a solution capable of essentially complete modification of the binding sites on the outer surfaces of the carrier material to form at least one surface modification $M_1$, the binding sites on the outer surfaces of the carrier material are modified essentially completely by reaction to form at least one surface modification $M_1$.

According to one embodiment of the present invention, the phrase "essentially complete modification" means that essentially all the binding sites present on a surface of the carrier material are reacted to form surface modifications $M_1$ and/or $M_2$ either on the outer surface or on the inner surface, and thus essentially no free or modifiable binding sites remain on the respective surface of the carrier material. To produce such an essentially complete modification, the respective reaction solutions preferably contain an excess of modifier.

The term "modification" as used herein may include altering, reacting, creating and/or destroying binding sites on the respective surface of the porous carrier material. According to a preferred embodiment, the term "modifying" includes the reaction of binding sites on the surfaces of the porous carrier material with, for example, nucleophiles or electrophiles to form surface modifications $M_1$ and/or $M_2$. Surface modifications $M_1$ according to the present invention preferably have the property of not interacting with blood, whereas surface modifications $M_2$ interact with substances present in the solution, suspension or dispersion, such as blood, to be separated.

After essentially completely modifying the binding sites on the outer surfaces of the carrier material to form at least one surface modification $M_1$, the reaction solution needed for the modification and then optionally also the medium, which is essentially not miscible with a solution capable of modification of the binding sites on the outer surfaces of the carrier material to form at least one surface modification $M_1$, are removed from the pores, e.g., by suction, heating, applying a vacuum for a prolonged period of time, if necessary and/or washing them out with another medium which is easily removed.

According to a preferred embodiment, the binding sites on the inner surfaces of the porous carrier material are modified after modification of the binding sites on the outer surfaces of the porous carrier material. If the reaction solution for the surface modification $M_2$ is miscible with the medium present in the pores, then the medium can remain in the pores and need not necessarily be removed, because by mixing the medium in the pores with the reaction solution for modifying the binding sites to form surface modifications $M_2$ and diffusion of this reaction solution into the pores, it is also possible to modify the binding sites in the pores. In most cases, however, it is preferable to first remove the medium from the pores. The inner surfaces of the carrier material are also preferably modified essentially completely to form at least one surface modification $M_2$.

According to another embodiment, surface modifications $M_2$ may also be present on the surfaces of the porous carrier material before modification of the binding sites on the outer surfaces to form surface modifications $M_1$. According to this embodiment, at first all binding sites on the inner and outer surfaces may, if necessary, be reacted to form surface modifications $M_2$. However, it is also possible for the binding sites of the carrier material to have the required binding properties of $M_2$ even without modification. Such a carrier material having $M_2$ groups, optionally modified, is provided as a carrier material in the method according to the present invention in the step of providing a porous particulate carrier material which has modifiable binding sites on the inner and outer surfaces. Then the following steps may be performed according to one embodiment of the method according to the present invention: filling the pores of the carrier material with at least one medium which is liquid under the conditions of filling and is essentially not miscible (under the modification conditions) with a solution with which binding sites on the surfaces of the carrier material can be modified essentially completely; modifying the binding sites on the outer surfaces of the carrier material essentially completely to form at least one surface modification $M_1$ and optionally removing the medium from the pores, this medium being essentially not miscible (under the modification conditions) with a solution with which the binding sites on the outer surfaces of the carrier material can be modified essentially completely, whereby in the step of modifying the binding sites on the outer surfaces of the carrier material essentially completely to form at least one surface modification $M_1$, the modification of the modifiable binding sites on the outer surfaces of the carrier material can also be performed, for example, by destroying the surface modifications $M_2$.

According to another embodiment, it is also possible to produce the adsorbent according to the present invention by reacting the binding sites on the outer surfaces of the carrier material essentially completely to form surface modifications $M_1$ after providing a porous particulate carrier material which has modifiable binding sites on the outer surfaces and the inner surfaces, this reaction being induced by essentially non-penetrating radiation, which does not penetrate through the carrier material. Since such radiation cannot penetrate into the pores, there is no reaction of the binding sites in the pores on the carrier material to form surface modifications $M_1$. Following that, binding sites on the inner surfaces of the carrier material may be reacted, to form surface modifications $M_2$, if necessary, this reaction being induced without the aforementioned radiation.

Thus, a method according to this embodiment includes the following steps:

providing a porous particulate carrier material which has on the outer surfaces and the inner surfaces modifiable binding sites, which can be reacted to form surface modifications $M_1$ and/or $M_2$, modifying the binding sites on the outer surfaces of the carrier material essentially completely, to form at least one surface modification $M_1$ by a reaction which is induced by a radiation that essentially does not penetrate through the carrier material, and optionally modifying the binding sites on the inner surfaces of the carrier material essentially completely to form at least one surface modification $M_2$ by a reaction which is not capable of modifying the surface modification $M_1$.

The radiation, which essentially does not penetrate through the carrier material, is preferably electromagnetic radiation in the UV or visible range.

According to this method, it is also possible for the porous carrier material which is provided to already have a modifiable surface modification $M_2$ on all surfaces, and for the modification of the binding sites on the inner surfaces to no longer be necessary after the essentially complete modification of the binding sites on the outer surfaces.

According to a preferred embodiment of the present invention, the porous carrier material described above, which can be modified to yield an adsorbent according to the present invention, can be produced, as mentioned above, by starting with certain polymerizable compounds by the suspension polymerization process described below.

This method of producing an adsorbent includes the following steps:

producing a porous particulate carrier material which has on its inner and outer surfaces modifiable binding sites, by suspension polymerization, whereby a hydrophobic phase comprising at least one monomer, at least one crosslinking agent, a pore-forming medium and a polymerization initiator is dispersed in a continuous phase comprising water and at least one protective colloid, and the monomers and crosslinking agents in the hydrophobic phase are polymerized, the pores of the resulting porous particulate carrier material being filled with the pore-forming medium, modifying the modifiable binding sites on the outer surfaces of the carrier materials essentially completely to form at least one surface modification $M_1$, and optionally removing the pore-forming medium from the pores.

According to another preferred embodiment of the present invention, the porous carrier material which can be modified to form an adsorbent according to the present invention can also be produced by the suspension polymerization process described below, wherein a water-soluble monomer is added to the aqueous continuous phase, so that the production of the porous particles of the carrier material and the modification of the outer surfaces of these particles are accomplished in one step.

This method of producing an adsorbent which is also preferred includes the following steps:

producing a porous particulate carrier material which has modifiable binding sites on the inner and outer surfaces, by suspension polymerization, whereby a hydrophobic phase comprising at least one monomer, at least one crosslinking agent, a pore-forming medium and a polymerization initiator is dispersed in a continuous phase comprising water, at least one protective colloid, and at least one water-soluble monomer which is essentially insoluble in the hydrophobic phase, whereby the monomers and crosslinking agents present in the hydrophobic phase are polymerized, forming a porous core, and the at least one water-soluble monomer in the phase interface between the hydrophobic phase and the continuous phase is polymerized to form at least one surface modification $M_1$, at least a portion of the polymer chains formed from the water-soluble monomer binding covalently to the porous core thus formed, and optionally removing the pore-forming medium from the pores.

In the suspension polymerization processes described above, protective colloids and/or stabilizers conventionally used in the technical field may be used in the aqueous continuous phase. Preferably one or more protective colloids from the group consisting of polyvinyl alcohol (PVA), polyvinylpyrrolidone (PVP) and polyethylene glycol are used.

The monomer present in the hydrophobic phase is preferably a monomer containing epoxy groups or a mixture of a monomer containing epoxy groups and at least one additional monomer. As described above, however, other monomers having a strained heterocyclic system as the functional group may also be used, e.g., aziridine groups or episulfide groups. The monomer containing the epoxy groups is preferably a (meth)acrylic acid monomer containing epoxy groups. The term "a (meth)acrylic acid monomer containing epoxy groups" as used herein is understood to refer mainly to such a monomer in which the moiety carrying the epoxy group is bound via the ester functionality of a substituted or unsubstituted (meth)acrylic acid. However, it is also possible for the moiety carrying the epoxy group to be bound to the (meth)acrylic acid monomer in some other manner, e.g., at one of the carbons of the C—C double bond. According to one preferred embodiment, the (meth)acrylic acid monomer containing epoxy groups is glycidyl (meth)acrylate.

In the suspension polymerization processes described above, a monomer having at least two polymerizable groups may be used as a cross-linking agent, leading to crosslinking of the growing polymer chains. The term "crosslinking agent" as used herein is understood to refer to conventional monomers used in a technical field, having at least two polymerizable groups, where the polymerizable groups may be, for example, vinyl groups, acrylate groups or methacrylate groups. Preferably a monomer based on (meth)acrylic acid is used as the monomer having at least two polymerizable groups. According to an especially preferred embodiment, the monomer having at least two polymerizable groups is ethylene glycol di(meth)acrylate. Furthermore, the two (meth)acrylate groups of such a monomer may also be joined by another linkage group derived from α,ω-diols, for example, or in general from alcohols having at least two OH groups. The amount of crosslinking agent, based on the monomer content in the hydrophobic phase, may be 5 to 95 percent by weight, preferably 20 to 60 percent by weight, and is preferably 40 percent by weight.

In the suspension polymerization processes described above, the pore-forming medium is a mixture of at least two components selected from linear, branched or cyclic alcohols with 5 to 14 carbons and esters of mono- or dicarboxylic acids with 2 to 10 carbons, esterified with monohydric or polyhydric alcohols having 1 to 6 carbons. One component of the pore-forming medium described above may be a linear, branched or cyclic (primary, secondary or tertiary) alcohol, with 5 to 14 carbons, e.g., hexanol, octanol, decanol or dodecanol. Another component of the pore-forming medium described above may be an ester of a mono- or dicarboxylic acid with 2 to 10 carbons esterified with monohydric or polyhydric alcohols having 1 to 6 carbons, e.g., butyl acetate, diethyl succinate or glycerol tributyrate. A mixture of two components is used as the pore-forming medium or pore-forming agent, whereby the resulting polymer is not soluble in any of the components, but one component dissolves the oligomer formed during suspension polymerization, and the other component is not capable of dissolving the resulting oligomer. Formation of pores is made possible by the specific choice of the components of the pore-forming medium. The method described above for producing pores in a polymer carrier material is known to those skilled in the art. Furthermore, in routine experiments, e.g., through a suitable choice of the pore-forming medium or by varying the ratio of components, it is possible to adjust the pore volume and the pore diameter in the desired manner. In this connection, the term "oligomer" as used herein is understood to refer to a material having a molecular weight up to approximately $10^4$ g/mol formed in a suspension polymerization process as described above. A mixture of dodecanol and cyclohexanol and/or a mixture of diethyl succinate and dodecanol is especially preferred as the pore-forming medium. The amount of pore-forming medium described above, based on the hydrophobic phase, may be from 20 to 90 percent by weight, preferably 40 to 80 percent by weight, and is preferably 70 percent by weight.

A polymerization initiator to be used in the suspension polymerization processes described above is in general not subject to any particular restrictions. For example, a polymerization initiator from the group of azo compounds, peroxides and redox initiators may be used. Preferably a suitable azo compound or a suitable peroxide is used as the polymerization initiator. The polymerization initiator is especially preferably azobisisobutyronitrile or dibepzoyl peroxide. The amount of polymerization initiator, based on the amount of monomer, may be from 0.1 to 5 percent by weight, preferably 0.5 to 2 percent by weight, and is preferably 1 percent by weight.

In the suspension polymerization process described above in which a water-soluble monomer is added to the aqueous continuous phase, the water-soluble monomer may be a monofunctional vinyl compound. The water-soluble monomer preferably has one or more polar groups. The water-soluble monomer is especially preferably selected from hydroxyalkyl methacrylates, aminoalkyl methacrylates, N-vinyl-2-pyrrolidone, acrylonitrile and methacrylonitrile, acrylic acid and methacrylic acid, allyl alcohol, allylamine, 3-allyloxy-1,2-propanediol, (ethylene glycol)$_n$-vinylmethyl ethers where n 1 to 10, N-methylol-acrylamide, 2-acrylamido-2-methylpropanesulfonic acid and salts of vinylbenzenesulfonic acid, vinylsulfonic acid, as well as combinations thereof. The preferred hydroxyalkyl methacrylates and/or aminoalkyl methacrylates are those having an alkyl group with 1 to 10 carbons, e.g., a methyl, ethyl, propyl or butyl group. It is even more preferable for the water-soluble monomer to be acrylic acid, N-vinyl-2-pyrrolidone or a combination thereof. The amount of water-soluble monomer may be 2 percent by weight to 80 percent by weight, based on the total starting weight of the monomer of the porous carrier material. The amount of water-soluble monomer is preferably 5 percent by weight to 50 percent by weight, based on the total starting weight of the monomer of the porous carrier material, and is preferably 20 to 30 percent by weight.

The present invention, according to one embodiment, also relates to the use of the adsorbent for separating biomolecules and/or pathogenic substances such as toxins from whole blood. For example, biomacromolecules such as LDL and endotoxins, immunoglobulins, fibrin, fibrinogens, immune complexes, exotoxins, fibronectins and/or superantigens may be removed.

Furthermore, the present invention provides for the use of the adsorbent according to the present invention for production of an adsorbent comprising a housing and an adsorbent therein for separating biomolecules and/or pathogenic substances from whole blood. An adsorber equipped with the adsorbent produced according to various embodiments of the present invention has a housing, which is preferably designed in the form of a tube or column and contains the adsorbent as a packing material. With regard to the quantities of blood which are usually to be processed and the efficiency of the adsorber according to the present invention, the adsorber preferably has a volume of 250 ml to 1250 ml. The adsorber may be used individually or in duplicate or in multiple instances in an operation. When there are two or more adsorbers, there is the possibility of charging one adsorber with the blood so as to alternate with another adsorber, which is being regenerated. This may lead to a greater efficiency in the use of the adsorbent produced according to the present invention. The adsorber containing the adsorbent is preferably designed so that it has a housing with an inlet area on the head end through which the blood is supplied to the adsorber, in this case the outlet being located on the bottom of the housing of the adsorber.

To prevent unwanted substances, e.g., substances originating from the adsorbent material, from being returned with the treated blood back to the patient's bloodstream, a filter is preferably provided at the outlet of the housing of the adsorber. It is preferably a particulate filter.

Various embodiment of the present invention will be explained further through the following examples.

EXAMPLES

Example 1

Reaction solution I: 75 mg CMECDI (2-morpholino-ethanesulfonic acid monohydrate) was dissolved at 4° C. in 200 ml 0.1 M MES (N-cyclohexyl-N'-(2-morpholinoethyl)-carbodiimide-methyl-p-toluenesulfate) with a pH of 4.75; 75 mg polyacrylic acid with a weight-average molecular weight of 800,000 was added, the pH was adjusted to 4.75 and the mixture was stirred for 0.5 hour at 4° C.

In a round-bottom flask, 75 ml carrier material particles (Eupergit C 250L) in 75 ml 25% $NH_3$ solution were stirred overnight. The carrier material particles were washed three times with water, decanted, filtered with suction, washed again with water and dried.

The carrier material particles were allowed to swell for 30 minutes in 100 ml n-hexane, then filtered with suction for 15 seconds on a suction filter, and next added immediately to the reaction solution I described above at 4° C., then agitated and stirred overnight at 4° C. Then the particles were filtered with suction, washed with water, 4 M NaCl and again with water and dried in a vacuum dessicator over $CaCl_2$.

40 ml of these particles was stirred for 2 hours at 40° C. together with 50 ml 0.25% glutardialdehyde solution. Then the particles were washed with 7.5 L water and dried with suction.

To 18 ml of a C1q solution was added 32 ml of a phosphate-buffered saline solution (PBS, 0.1 M $NaH_2PO_4$, 0.154 M NaCl, pH 6.8) and the UV absorption at 280 nm was measured. The absorption measured at 280 nm was 1.040, corresponding to a concentrate of 1.53 g/L (reaction solution II).

To this solution were added the particles treated with reaction solution I, the mixture was stirred for three hours at room temperature and then filtered with suction. The solution had a UV absorption of 0.577 at 280 nm, corresponding to a concentration of 0.85 g/L. The coupling yield of the reaction solution II was thus 0.68 g/L.

Then the particles were washed with 600 ml PBS, stirred twice in 200 ml 5 mM ascorbic acid in PBS, each time for one hour at room temperature, and filtered with suction. The particles were stirred for four hours in 1 M ethanolamine in PBS at a pH of 8 at room temperature and filtered with suction. Then the particles were stirred again twice in 200 ml 5 mM ascorbic acid in PBS each for one hour at room temperature and filtered with suction. Next the particles were washed with the following solutions:

1. 400 ml, 0.1 M acetate, 0.5 M NaCl, pH 4
2. 400 ml, 1 M $NaH_2PO_4$, 0.5 M NaCl, pH 9
3. 400 ml, 0.1 M $NaH_2PO_4$, 0.154 M NaCl, pH 6.8
4. 2 L, 0.154 M NaCl.

Finally, the particles were autoclaved for 20 minutes at 121° C. in 0.154 M NaCl for heat sterilization.

Examples 2 Through 6

Adsorbent materials were produced in the same way as described in Example 1, using the medium, the surface modifications, etc. as listed in Table 1.

For comparison purposes, adsorbents having C1q (Comparative Example 1), PAA (Comparative Example 2) or OH groups (Comparative Example 3) as surface modifications on both the inner and outer surfaces were produced for comparison purposes.

TABLE 1

| | $M_1$ | $M_2$ | Carrier material | Method (medium) | CMECDI activation |
|---|---|---|---|---|---|
| Ex. 1 | PAA | C1q | Beads 1 | I (hexane) | no |
| Ex. 2 | PAA | C1q | Beads 1 | I (dodecanol) | no |
| Ex. 3 | PAA | C1q | Beads 1 | I (hexane) | yes |
| Ex. 4 | PAA | C1q | Beads 1 | I (dodecanol) | yes |
| Ex. 5 | PAA | C1q | Beads 2 | I (hexane) | yes |
| Ex. 6 | PAA | C1q | Beads 2 | I (dodecanol) | yes |
| Comp. Ex. 1 | C1q | C1q | Beads 1 | — | — |
| Comp. Ex. 2 | PAA | PAA | Beads 1 | — | — |
| Comp. Ex. 3 | OH | C1q | Beads 1 | — | — |

Notes:
All beads had an average pore size between 100 and 200 nm.
Eupergit 250 L was used for beads 1.
Beads 2 were made of a random copolymer produced by polymerization of ethylene glycol di(meth)acrylate and glycidyl methacrylate and allylglycidyl ether.

The results of the tests with regard to the binding capacity for platelets and/or immune complexes are shown in Table 2.

TABLE 2

| | | | Binding capacity for | |
|---|---|---|---|---|
| | $M_1$ | $M_2$ | Immune complexes | platelets |
| Ex. 1 | PAA | C1q | yes | no |
| Ex. 2 | PAA | C1q | yes | no |
| Ex. 3 | PAA | C1q | yes | no |
| Ex. 4 | PAA | C1q | yes | no |
| Ex. 5 | PAA | C1q | yes | no |
| Ex. 6 | PAA | C1q | yes | no |
| Comp. Ex. 1 | C1q | C1q | yes | yes |
| Comp. Ex. 2 | PAA | PAA | no | no |
| Comp. Ex. 3 | OH | C1q | yes | yes |

It can be seen from this Table 2 that all the absorbers according to the present invention as described in Examples 1 through 6 have a binding capacity for immune complexes but do not interact with platelets. An adsorbent which also has C1q surface modifications on the outer surfaces would also filter platelets out of whole blood in addition to immune complexes (Comparative Example 1), so this adsorber may not be suitable for purifying whole blood. An adsorbent having only PAA as the surface modification (Comparative Example 2) was compatible with whole blood but did not have any binding sites for immune complexes, so immune complexes were not separated. An adsorbent having OH groups as surface modification $M_1$ had a weak interaction with platelets. For this reason, a surface modification $M_1$ which is different from an OH group is preferred according to the present invention.

Example 7

Step A (Producing a Porous Carrier Material by Suspension Polymerization)

A porous carrier material is produced, for example, according to European Patent Application No. 0 495 107 A1 by suspension polymerization. The resulting carrier material (beads) is filtered out from the mother liquor at an excess pressure of 0.5 bar within 30 s.

Step B (Amination of the Outer Surface of the Carrier Material)

100 g wet carrier material from step A was incubated for three hours at room temperature on a rotary agitator together with 300 ml 25 percent by weight ammonia (Fluka). Then the reaction solution was filtered at an excess pressure of 0.5 bar to separate the carrier material, which was washed with distilled water until neutral.

Step C (Modification of the Outer Surface of the Carrier Material with a Surface Modification MO 25 g of a 10 percent by weight polyacrylic acid solution (Degapas 11105S, Stockhausen Company) was dissolved in 175 g of an isotonic NaCl solution, adjusted to a pH of 4.75 and incubated on a rotary agitator with a solution of 1.25 g N-(3-dimethylaminopropyl)-N'-ethyl carbodiimide hydrochloride (Fluka) in 50 ml of an isotonic NaCl solution for 45 minutes at room temperature.

Then the carrier material filtered out of the solution from step B was added to this solution and incubated for four hours at room temperature on a rotary agitator.

Step D (Washing out the Pore Space of the Carrier Material)

After suction filtration of the modification solution described above, the carrier material was washed once with 600 ml of a 0.05 M sodium hydroxide solution in 50% isopropanol, four times with 600 ml isopropanol and twice with 600 ml distilled water.

Step E (Amination of the Inner Surface of the Carrier Material)

Amination of the inner surface of the carrier material obtained according to step D was performed by analogy with step B, but using 12.5% ammonia at 40° C. (reaction time four hours).

Step F (Coupling the Amino Groups to the Surface Modification

The carrier material from step E was washed four times with 250 ml $NaH_2PO_4$ buffer (pH 6.8) (PP buffer). Then the carrier material was incubated for two hours at 40° C. with 300 ml of a 0.4% glutardialdehyde solution (Fluka) in PP buffer on a rotary agitator, washed 12 times with 1 L distilled water each time and equilibrated 4 times with 1 L PP buffer to pH=6.8. Then the glutardialdehyde groups were reacted with 300 ml of an ethanolamine solution (Fluka) in distilled water at a pH of 8 (four hours, room temperature, rotary agitator), and the carrier material was washed four times with 250 ml PP buffer each time. Then the carrier material was incubated for four hours at room temperature on a rotary agitator (in the dark) together with 250 ml of a 5 mM ascorbic acid solution (Fluka) in PP buffer and washed with 500 ml of each of the following:

0.1 M sodium acetate buffer, pH 4.6, in isotonic NaCl solution 0.1 M sodium phosphate buffer, pH 9, in isotonic NaCl solution 0.1 M sodium phosphate buffer, pH 7.4, in isotonic NaCl solution isotonic NaCl solution (4 times)

and then autoclaved for 20 minutes at 121° C.

Example 8

A porous carrier material was prepared in the same manner as described in Example 7, except that step D was performed before step C.

Comparative Examples 4 and 5

For comparison purposes, adsorbents were prepared as described in Example 7, but they were modified on both the inner and outer surface exclusively with surface modification $M_1$ (Comparative Example 4) or exclusively with surface modification $M_2$ (Comparative Example 5).

Table 3 summarizes the results of tests of the binding capacity for platelets and fibrinogen.

TABLE 3

| | Surface of the carrier material | | Binding capacity for | |
|---|---|---|---|---|
| | Outside | Inside | Platelets | Fibrinogen |
| Ex. 7 | $M_1$ | $M_2$ | no | yes |
| Ex. 8 | $M_1$ | $M_2$ | no | yes |
| Comp. Ex. 4 | $M_1$ | $M_1$ | no | no |
| Comp. Ex. 5 | $M_2$ | $M_2$ | yes | yes |

Example 9

Producing a Porous Carrier Material by Suspension Polymerization in the Presence of a Water-Soluble Monomer in the Aqueous Phase 1.5 g polyvinyl alcohol (W25/190, Erkol) and 744 g distilled water were stirred until dissolved in a double-jacketed glass reactor equipped with a 4-blade paddle stirrer. Then a solution consisting of 135 g cyclohexanol, 13 g dodecanol (Fluka), 40 g ethylene glycol dimethacrylate (Röhm, Darmstadt), 60 g glycidyl methacrylate (Transol) and 1.1 g azobisisobutyronitrile (Vazo 64, DuPont) was added. The reaction mixture was stirred for 30 minutes at 270 rpm and then heated to 65° C. to initiate polymerization. On reaching a temperature of 60° C., 19 g acrylic acid (Merck) was added to the reaction mixture. After another five hours at 65° C. and four hours at 78° C., the mixture was heated to 91° C. for 1.5 hours. After cooling to room temperature, the bead polymer thus formed was filtered out, washed repeatedly with isopropanol (12 times with 400 ml) and fractionated.

100 g of the moist carrier material formed as described above was incubated for three hours at room temperature on a rotary agitator together with 25 percent by weight ammonia (Fluka). Then the reaction solution was filtered at an excess pressure of 0.5 bar to separate the carrier material, which was washed with distilled water until neutral.

The carrier material described above was washed 4 times with 250 ml NaH$_2$PO$_4$ buffer (pH=6.8) (PP buffer). Then the carrier material was incubated for two hours at 40° C. together with 300 ml of a 0.4% glutardialdehyde solution (Fluka) in PP buffer on the rotary agitator, washed 12 times with 1 L distilled water each time and equilibrated 4 times with 1 L PP buffer to pH 6.8. Then the glutardialdehyde groups were reacted with 300 ml of a 0.25 M ethanolamine solution (Fluka) in distilled water at a pH of 8 (four hours, room temperature, rotary agitator) and the carrier material thus formed was washed 4 times with 250 ml PP buffer each time. The carrier material was then incubated for four hours at room temperature on the rotary agitator (in the dark) together with 250 ml of a 5 mM ascorbic acid solution (Fluka) in PP buffer and washed with 500 ml of each of the following:

0.1 M sodium acetate buffer, pH 4.6, in isotonic NaCl solution 0.1 M sodium phosphate buffer, pH 9, in isotonic NaCl solution 0.1 M sodium phosphate buffer, pH 7.4, in isotonic NaCl solution isotonic NaCl solution (4 times)

and then autoclaved for 20 minutes at 121° C.

Comparative Example 6

For comparison purposes, a porous carrier material was prepared as described in Example 9, except that no acrylic acid was added to the reaction mixture (e.g., to the reaction phase).

Comparative Example 7

For comparison purposes a support material was prepared as described in Example 9 and was treated with polyacrylic acid on the inner and outer surfaces of the porous carrier material.

Table 4 summarizes the results of tests to determine, the platelet and fibrinogen binding capacity of the porous carrier materials produced according to Example 9 and Comparative Examples 6 and 7.

TABLE 4

| | Type of surface modification | Binding capacity for | |
| --- | --- | --- | --- |
| | | Platelets | Fibrinogen |
| Ex. 9 | with polyacrylic acid on the outer surface of the beads | no | yes |
| Comp. Ex. 6 | without polyacrylic acid on the outer surface of the beads | yes | yes |

TABLE 4-continued

| | Type of surface modification | Binding capacity for | |
| --- | --- | --- | --- |
| | | Platelets | Fibrinogen |
| Comp. Ex. 7 | comparative material with polyacrylic acid on the inner and outer surfaces of the beads | no | no |

What is claimed is:

1. An adsorbent for whole blood in the form of essentially spherical nonaggregated particles comprising:

having pore sizes configured to allow configured to separate low density lipoproteins, immunoglobulins, fibrins, fibrinogens, immune complexes, fibronectins, or superantigens from whole blood to enter the pores, said porous carrier material having:

an average pore size of 0.3 µm to ≦1.5 µm, whereby a maximum of about 50% of the pore volume of the organic porous carrier material is present in the form of pores having a pore size of >1.5 µm, an outer surface of the porous carrier material having at least one outer surface modification that does not interact with blood cells, and an inner surface of the porous carrier material having at least one inner surface modification that interacts with substances contained in blood, wherein the at least one outer surface modification is different from the at least one inner surface modification, wherein the porous carrier material has modifiable binding sites on its outer and inner surfaces, wherein at least one outer surface modification is by covalent bonding of at least one first functional group to the binding sites on the outer surface, wherein the at least one first functional group is at least one of poly(carboxylic acid), albumin, heparin, heparan sulfate and/or polymyxin, wherein the at least one inner surface modification is by covalent bonding of at least one second functional group to the binding sites on the inner surface, and wherein the at least one second functional group is selected from the group consisting of the complement factor C1q, peptides, antibodies and antigens.

2. The adsorbent according to claim 1, whereby the particles of the adsorbent have a particle size of 50 to 500 µm.

3. The adsorbent according to claim 1, whereby the at least one first functional group is selected from polyacrylic acid and/or heparin.

4. The adsorbent according to claim 1, whereby the at least one second functional group is an immunoadsorbent.

5. The adsorbent according to claim 1, whereby the carrier material is a copolymer derived from (meth)acrylate esters and/or amides.

6. The adsorbent according to claim 5, whereby the copolymer derived from (meth)acrylate esters and/or amides has epoxy groups.

7. The adsorbent according to claim 5, whereby the copolymer is a random copolymer formed by polymerization of ethylene glycol di(meth)acrylate and glycidyl (meth)acrylate and/or allylglycidyl ether.

8. The adsorbent according to claim 5, whereby the copolymer is a cross-linked random copolymer produced by polymerization of the monomer units
- (A) (meth)acrylamide in an amount of 10 to 30 wt %,
- (B) N,N'-methylene bis(meth)acrylamide in an amount of 30 to 80 wt %, and
- (C) allylglycidyl ether and/or glycidyl (meth)acrylate in an amount of 10 to 20 wt %, each based on the total weight of the monomer units.

9. The adsorbent according to claim 5, whereby the copolymer has been produced by suspension polymerization.

10. The adsorbent of claim 1, wherein the antibodies are selected from the group comprising: monoclonal or polyclonal anti-fibrinogen or anti-fibrin antibodies.

11. The adsorbent of claim 1, wherein the antigens are synthetic A/B blood group antigens.

12. The adsorbent according to claim 1, wherein the at least one inner surface modification is incompatible with blood cells.

13. The adsorbent according to claim 1, wherein the second functional group is chosen from the group of separation effectors, catalysts, or enzymes.

14. The adsorbent according to claim 1, wherein the average pore size of the organic porous carrier material is about 1.5 µm.

15. The adsorbent according to claim 1, wherein the average pore size of the organic porous carrier material is about 1.0 µm.

16. The adsorbent according to claim 1, wherein the average pore size of the organic porous carrier material is about 0.5 µm.

17. The adsorbent according to claim 1, wherein the average pore size of the organic porous carrier material is about 0.3 µm.

* * * * *

UNITED STATES PATENT AND TRADEMARK OFFICE
CERTIFICATE OF CORRECTION

PATENT NO. : 7,838,306 B2
APPLICATION NO. : 10/380193
DATED : November 23, 2010
INVENTOR(S) : Hanno Baumann et al.

It is certified that error appears in the above-identified patent and that said Letters Patent is hereby corrected as shown below:

In the Claims

Column 18, lines 17 to 18, please change "having pore sizes configured to allow configured to separate low density lipoproteins" to --an organic porous carrier material having pore sizes configured to allow low density lipoproteins--

Signed and Sealed this
Second Day of July, 2013

Teresa Stanek Rea
*Acting Director of the United States Patent and Trademark Office*